United States Patent [19]

Jessel, Jr. et al.

[11] Plant 4,218

[45] Mar. 7, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 778,667

[22] Filed: Mar. 17, 1977

[51] Int. Cl.[2] ..... A01H 5/00

[52] U.S. Cl. ..... Plt./77

[58] Field of Search ..... Plt./76, 77

*Primary Examiner*—Robert E. Bagwill
*Attorney, Agent, or Firm*—Donald D. Jeffery

[57] ABSTRACT

A spider chrysanthemum characterized by its white ray florets and ability to be flowered throughout the year.

3 Drawing Figures

The present invention comprises a new and distinct cultivar of *Chrysanthemum morifolium* Ramat., hereinafter referred to by the cultivar name Splash (#73038048).

Splash is a product of a planned breeding program which had the objective of creating new chrysanthemum cultivars with spider capitulum type, with white ray floret color, with 9 and/or 10 week flowering response, and with the ability to produce commercially acceptable quality in year round cut mum programs. Such traits in combination were not present in previously available commercial cultivars.

Splash was originated from a cross made in a controlled breeding program in Barberton, Ohio in 1972. The female parent was White Spider 2275 (#21660E02; unpatented; commercially available), a white spider. The male parent was Yellow Daisy Pot (#2168AE01; unpatented; commercially available), a yellow spooned daisy sport of White Daisy Pot (#21680E01; unpatented; commercially available). The parentage of White Spider 2275 and White Daisy Pot is unknown to the present inventors.

Splash was discovered and selected as one flowering plant within the progeny of the stated cross by Walter H. Jessel, Jr. and William E. Duffett on Mar. 26, 1973 in a controlled environment in Barberton, Ohio.

The first act of asexual reproduction of Splash was accomplished when vegetative cuttings were taken from the initial selection in May, 1973 in a controlled environment in Barberton, Ohio, by a technician working under formulations established and supervised by Walter H. Jessel, Jr. and William E. Duffett. Horticultural examination of selected units initiated Feb. 18, 1975 has demonstrated that the combination of characteristics as herein disclosed for Splash are firmly fixed and are retained through successive generations of asexual reproduction.

Splash has not been observed under all possible environmental conditions. The phenotype may vary significantly with variations in environment such as temperature, light intensity, and daylength. The following observations, measurements, and comparisons describe plants grown in Barberton, Ohio under greenhouse conditions which approximate those generally used in commercial practice, as described in Chart A which appears at the end of the present specification. A light intensity chart of general use is shown in ASHAE Trans., Vol. 64, pg. 64 and reference is made thereto.

The following traits have been repeatedly observed and are determined to be basic characteristics of Splash which in combination distinguish this chrysanthemum as a new and distinct cultivar:

1. Flat capitulum form, reflexing slightly at full maturity.
2. Spider capitulum type.
3. Ivory white ray floret color.
4. Diameter across face of inflorescence ranging from 100 to 115 mm. at maturity.
5. Uniform 10 week photoperiodic flowering response to short days.
6. Tall plant height (requiring 2 to 4 long day weeks prior to short days to attain a flowered plant height of 72 to 82 cm. for November through April flowerings).
7. Semi-upright branching pattern.

The accompanying photographic drawings show typical inflorescence and foliage characteristics of Splash with colors being as nearly true as possible with illustrations of this type. Sheet 1 is a color photograph of Splash. Sheet 2 is a black and white photograph showing three views of the inflorescence of Splash. Sheet 3 is a black and white photograph showing the foliage of Splash at three stages of growth.

Of the many commercial cultivars known to the present inventors, the most similar existing cultivar in comparison to Splash is the maternal cultivar, White Spider 2275. Reference is made to attached Chart B which compares certain characteristics of Splash to those same characteristics of White Spider 2275. It will be noted that Splash has smaller diameter across face of capitulum, taller plant height, and longer flowering response period than White Spider 2275. The ray floret color, capitulum form, and capitulum type of Splash are similar to those same characteristics of White Spider 2275.

In the following description, color references are made to The Munsell Color Cascade, 1972 edition. The color values were determined between 2:00 and 2:30 P.M. on Nov. 12, 1976 under 150 foot-candle light intensity at Barberton, Ohio.

Botanical classification: *Chrysanthemum morifolium*, Ramat., cv Splash.

INFLORESCENCE

Capitulum (See Sheets 1 and 2 of drawings):

*Form.*—Flat, reflexing slightly with age.

*Type.*—Spider.

*Permanence.*—14 to 18 days.

*Diameter across face.*—100 to 115 mm.

Corolla of ray florets:

*Color* (*adaxial*).—Approximately 21-15 overlaid with white.

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7-10 f.c. | To Sept. 15 on - 5:30 PM Off - 7:30 AM | From Oct. 15 300 ppm |
| WINTER | 58° F to 62° F | 65° F to 70° F | 60° F to 65° F | 2 to 5 weeks at 5 hours Per Night of 7-10 f.c. | NONE | 300 ppm |
| SPRING | 58° F to 65° F | 65° F to 80° F | 60° F to 75° F | 2 to 4 weeks at 5 Hours Per Night of 7-10 f.c. | From Mar. 15 on - 5:30 PM Off - 7:30 AM | To Apr. 15 300 ppm |
| SUMMER | 62° F to 68° F | 70° F to 90° F | 65° F to 75° F | 1 to 2 weeks at 3 Hours Per Night of 7-10 f.c. | on - 6:00 PM Off - 8:00 AM | NONE |

CHART B

COMPARISON OF SPLASH AND WHITE SPIDER

| CULTIVAR | RAY FLORET COLOR | CAPITULUM FORM AND TYPE | DIAMETER ACROSS FACE OF CAPITULUM | PLANT HEIGHT | FLOWERING RESPONSE PERIOD |
|---|---|---|---|---|---|
| SPLASH | Ivory white | Flat spider | 100 to 115 mm. | Tall | 10 week |
| WHITE SPIDER 2275 | Ivory white | Flat spider | 130 to 175 mm. | Short | 10 week |

COMPARISONS MADE OF PLANTS GROWN AS SINGLE STEM CUT SPRAYS IN BARBERTON, OHIO UNDER CONDITIONS AS DESCRIBED IN CHART A.

*Persistence.*—Resists shatter.

*Color* (*abaxial*).—25-3 to white.

*Color* (*adaxial*).—25-1 to white.

Reproductive organs:

*Androecium.*—Present disc florets only; scant to numerous; scant pollen.

*Gynoecium.*—Present both ray and disc florets.

PLANT

General appearance: semi-upright branching pattern; tall height.

Foliage (See Sheets 1 and 3):

*Color* (*abaxial*).—Approximately 20-15.

We claim:

1. A new and distinct cultivar of *Chrysanthemum morifolium* Ramat., plant known by the cultivar name Splash and particularly characterized as to uniqueness by the combined characteristics of flat capitulum form, reflexing slightly at full maturity; spider capitulum type; ivory white ray floret color; diameter across face of capitulum ranging from 100 to 115 mm. at maturity; uniform 10 week photoperiodic flowering response to short days; tall plant height when grown as a single stem cut spray; and semi-upright branching pattern.

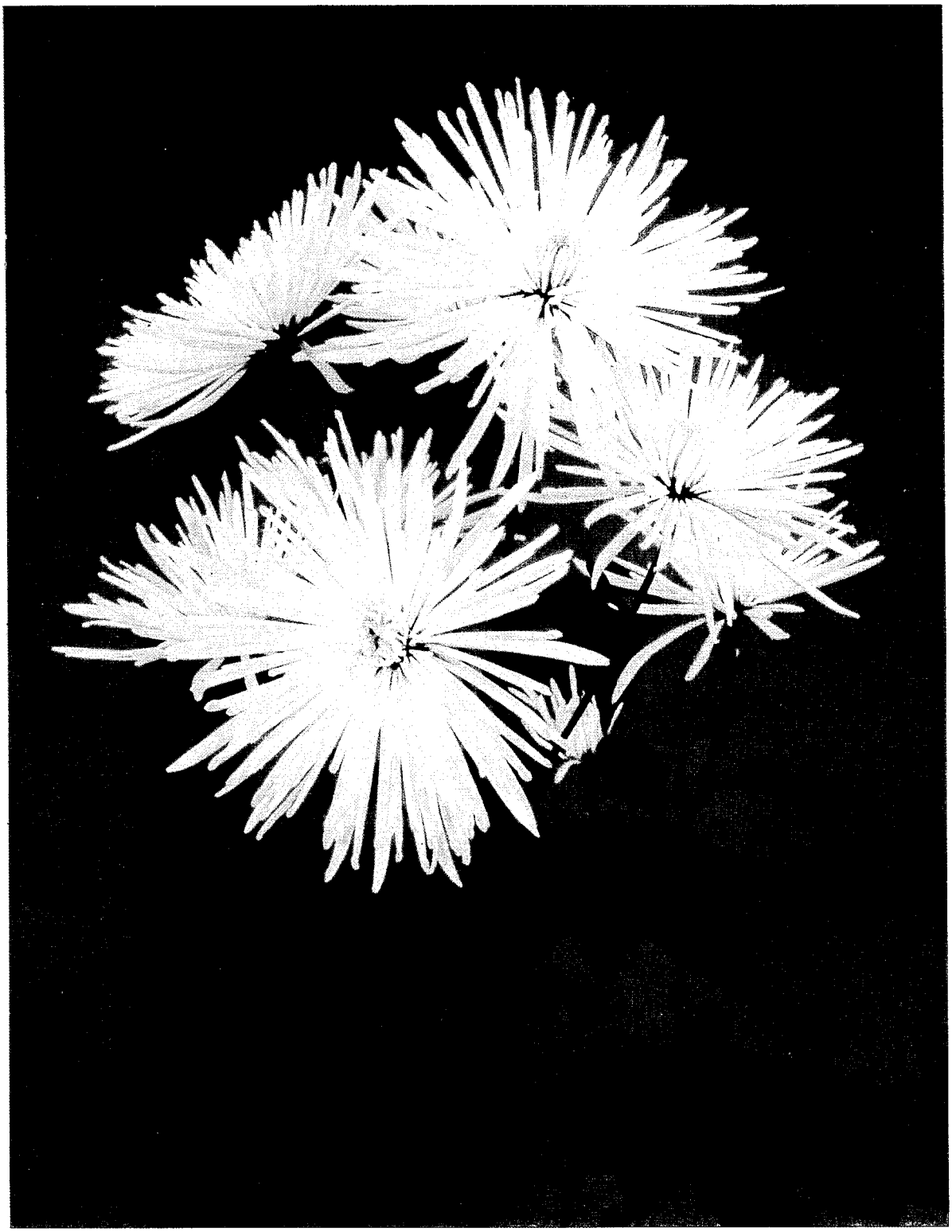

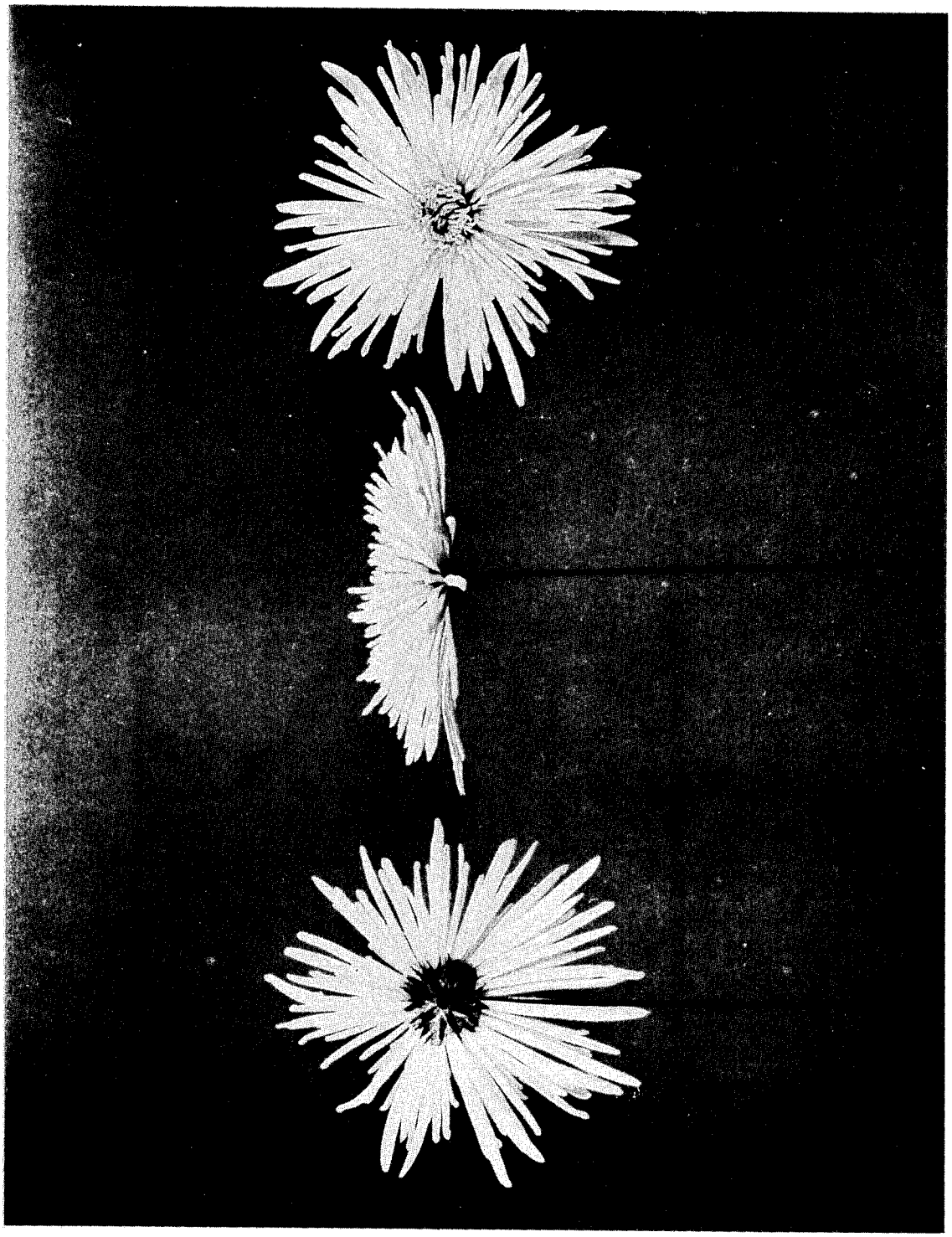

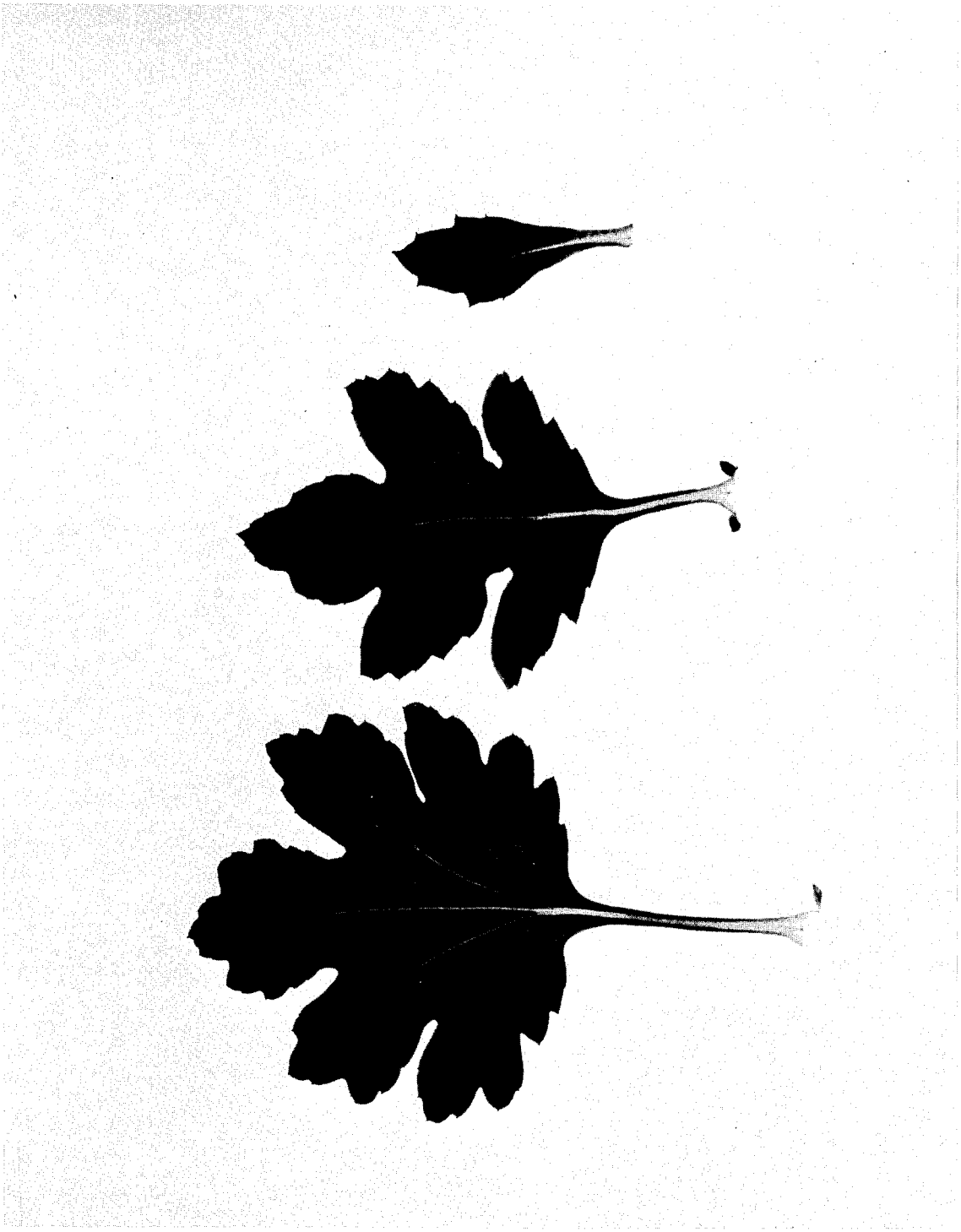

* * * * *